(12) United States Patent
Boutaud

(10) Patent No.: US 10,442,679 B2
(45) Date of Patent: Oct. 15, 2019

(54) BIOCOMPATIBLE MONOLITHICALLY INTEGRATED SENSOR, IN PARTICULAR FOR AN ACTIVE IMPLANTABLE MEDICAL DEVICE

(71) Applicant: MISTIC, Issy les Moulineaux (FR)

(72) Inventor: Bertrand Boutaud, Paris (FR)

(73) Assignee: MISTIC, Issy les Moulineaux (FR)

( * ) Notice: Subject to any disclaimer, the term of this patent is extended or adjusted under 35 U.S.C. 154(b) by 0 days.

(21) Appl. No.: 16/167,904

(22) Filed: Oct. 23, 2018

(65) Prior Publication Data

US 2019/0119100 A1  Apr. 25, 2019

(30) Foreign Application Priority Data

Oct. 24, 2017 (FR) .................................... 17 60013

(51) Int. Cl.
*B81B 3/00* (2006.01)
*G01L 9/00* (2006.01)
*A61B 5/0215* (2006.01)
*B81B 7/00* (2006.01)

(52) U.S. Cl.
CPC .......... *B81B 3/0021* (2013.01); *A61B 5/0215* (2013.01); *B81B 7/0058* (2013.01); *G01L 9/0042* (2013.01); *G01L 9/0072* (2013.01); *G01L 9/0073* (2013.01); *A61B 2562/028* (2013.01); *A61B 2562/0247* (2013.01); *B81B 2201/0264* (2013.01); *B81B 2207/015* (2013.01)

(58) Field of Classification Search
CPC ................ B81B 3/0021; B81B 7/0058; B81B 2201/0264; B81B 2207/015; A61B 5/0215; A61B 2562/028; A61B 2562/0247; G01L 9/0072; G01L 9/0042; G01L 9/0073
See application file for complete search history.

(56) References Cited

U.S. PATENT DOCUMENTS

2001/0054315 A1   12/2001   Aigner et al.
2011/0314922 A1   12/2011   Salleh et al.
2012/0096944 A1    4/2012   Leclerc

*Primary Examiner* — Anthony Ho
(74) *Attorney, Agent, or Firm* — Steven M. Greenberg, Esq.; Shutts & Bowen LLP

(57) ABSTRACT

The sensor includes: a first biocompatible substrate, with an operative area deformable under the effect of an external mechanical stress and a mobile transducer element; a second biocompatible substrate, with an operative area and a fixed transducer element cooperative with the mobile element to vary an electrical parameter of the sensor; a mechanical connection for securing the first substrate to the second substrate; a first sensor terminal coupled to the mobile element; and a second sensor terminal coupled to the fixed element. The operative area of one of the substrates has the shape of an islet of closed contour, physically and electrically isolated from the remainder of the substrate by a peripheral lateral layer that is monolithically integrated with the remainder of the substrate and the operative area.

14 Claims, 7 Drawing Sheets

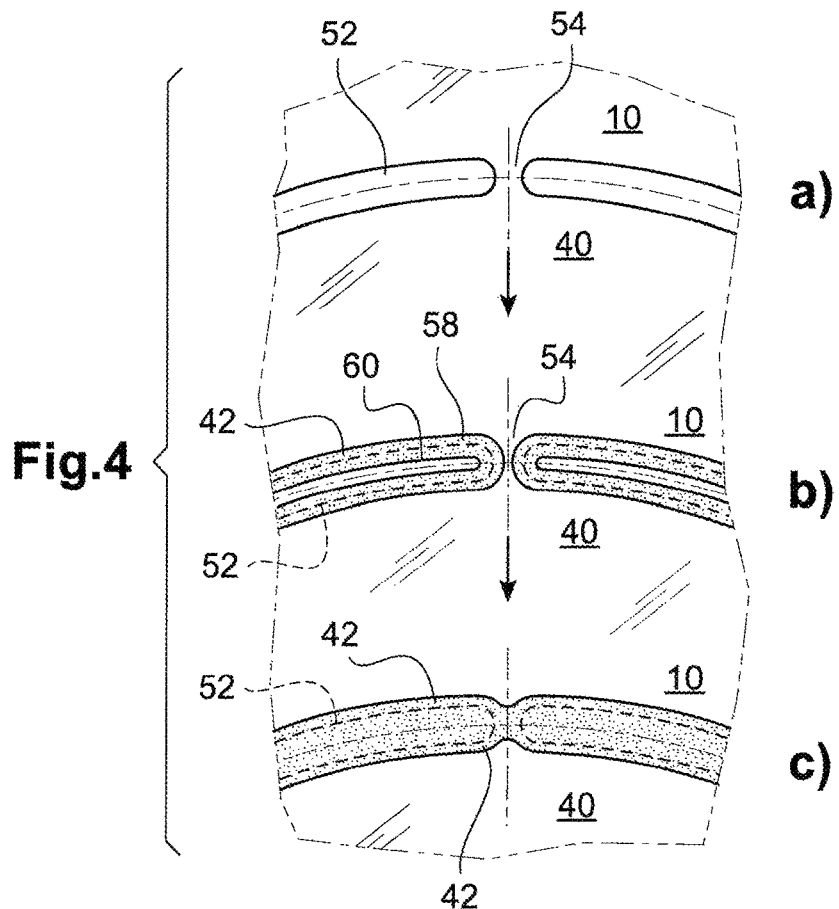
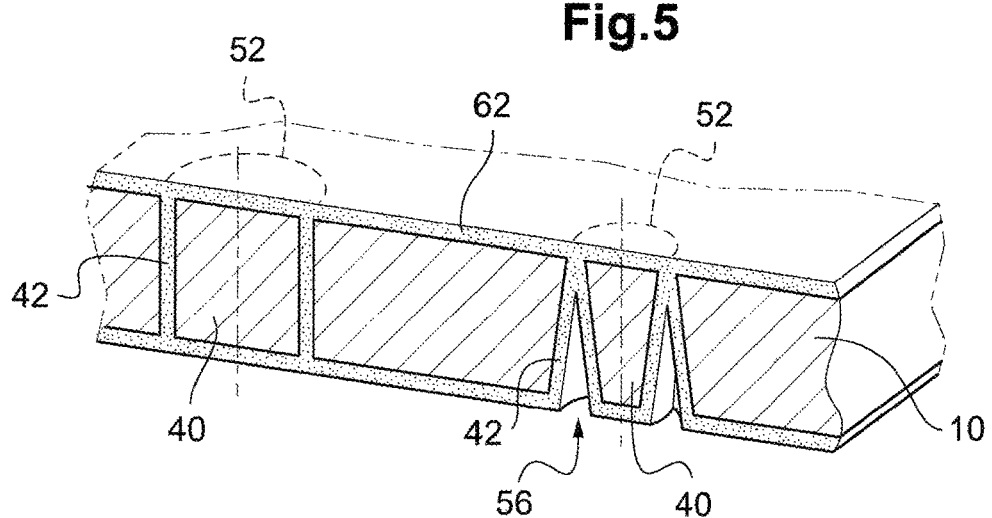

BIOCOMPATIBLE MONOLITHICALLY INTEGRATED SENSOR, IN PARTICULAR FOR AN ACTIVE IMPLANTABLE MEDICAL DEVICE

CROSS REFERENCE TO RELATED APPLICATIONS

This application claims priority under 35 U.S.C. § 119(a) to French Patent Application Serial Number 1760013, filed Oct. 24, 2017, the entire teachings of which are incorporated herein by reference.

BACKGROUND OF THE INVENTION

Field of the Invention

The invention relates to monolithically integrated sensors, in particular such sensors which include as a sensitive element a member that is mobile under an external stress depending on the quantity to be measured.

Description of the Related Art

Monolithically integrated sensors may be of very different natures: pressure sensors in which the surrounding medium exerts on a membrane a pressure that more or less deforms this membrane, acceleration sensors in which an inertial mass, integrated or added, more or less stresses a deformable structure, microphonic sensors in which the acoustic waves are collected and transformed into mechanical vibrations of a membrane that is integrated to the sensor, etc. In all cases, the variation of the quantity to be measured translates into a geometric deformation, that may for example induce a variation of the relative distance between two transducer elements, the transducer generally including a mobile element linked to the membrane or another deformable member, and a fixed element linked to the sensor body.

This distance variation is converted within the sensor into a variation of an electrical parameter, measurable by various techniques well known per se, such as capacitive measurement (the two transducer elements being opposite electrodes of a variable capacitor), resistive measurement (the electrodes establishing successive contacts as the deformation of the mobile member goes along), etc. The geometric deformation may also be directly converted into an electric potential variation through a piezoelectric layer that is associated with the deformable member and deformed in the same time as the latter. The electrical parameter variations collected by these various means are found at the sensor output terminals, which are connected, for example, to an analog/digital converter, a data processor, a filtering stage, etc., of the device.

Of note, sensors used for medical field applications are sensors made of a silicon substrate, a material that has for drawback that it is not recognized as biocompatible. Such sensor structures can hence not be implanted directly into the human body in contact with the corporeal fluids and the internal tissues of the patient. They imperatively require a protective encapsulation by an envelope made of a biocompatible material, with the particular difficulty that the encapsulation must allow the deformation of a sensitive element of the sensor at the level of the biocompatible material. This deformation of the envelop must then be transmitted to the silicon membrane (or another deformable member) of the sensor itself, to be detected by the transducer. This transmission is made through various mechanical means such as a linking rod or a fluid filling a buffer cavity between the biocompatible material and the silicone membrane.

Patent Cooperation Treaty (PCT) published request WO 2011/004113 A1 (FR 2 947 629 A1) and United States Patent Application Publication No. US 2006/0247539 A1 each describe examples of implantable sensors implementing technologies of this type. United States Patent Application Publication No. US 2008/0082005 A1 describes another sensor technique, which uses an antenna integrated in a biocompatible and mobile substrate whose deformation modifies the LC parameters of the antenna, with an external circuit converting this deformation into a variation of frequency. The dimensions required for such a deformable antenna are however an obstacle to a miniaturization of the sensor, and it is moreover necessary to protect the sensor by external means such as filters against high magnetic fields that may be undergone by the device when the patient is subjected to an examination in a MRI imaging device.

These structures of the state of the art are all complex, and are far from being optimum both in terms of industrialization costs and of possibilities of miniaturization.

BRIEF SUMMARY OF THE INVENTION

The invention described herein overcomes the foregoing difficulties by a sensor structure that may be made in particular (but not necessarily) of a material that is biocompatible, biostable and resistant to corrosion. In other words, the matter is to directly make the sensor from a material that can be placed directly in contact with the corporeal fluids and tissues, and that during the whole lifetime of the implanted device, typically during about ten years.

Thus, a first object of the invention is to propose for the sensors of this type, an entirely monolithically integrated structure making it possible to increase the degree of integration, while keeping the indispensable qualities of mechanical strength, electrical isolation and simplicity of the making processes by using only conventional and well-controlled techniques that are easy to industrialize on a large scale. Another object of the invention is to propose such a sensor structure that is usable in the medical field, with the constraints peculiar to this sector. The invention has also for object to propose such a sensor structure that can be made by means of conventional and well-controlled technologies, and hence with low industrialization costs.

Still another object of the invention is to propose a sensor structure that makes an extreme miniaturization of the component possible. This aspect is particularly important in the case of the implanted medical devices, especially certain devices such as the so-called leadless endocavitary autonomous capsules, which are entirely implanted into a cardiac cavity, as well as in case of integration into a cardiac lead of very reduced diameter. For that purpose, the invention proposes a sensor including, in a manner known per se:
  a first substrate made of a conductive material with an outer face and an inner face, including an operative area deformable under the effect of a mechanical stress applied to the outer face and, on the inner face of the operative area, a first transducer element, mobile under the effect of the deformation of the operative area;
  a second substrate made of a conductive material with an outer face and an inner face facing the inner face of the first substrate, and including an operative area;
  a second transducer element adapted to cooperate with the first transducer element to vary an electrical parameter between the first and the second transducer element under the effect of the mechanical stress;

a mechanical connection for securing the first substrate to the second substrate, located outside the operative areas;

a first sensor terminal, electrically coupled to the first transducer element; and a second sensor terminal, electrically coupled to the second transducer element.

Characteristic of the invention, for at least one of the substrates:

the operative area extends transversally into the thickness of the substrate, from one face to the other of the latter;

the operative area has the shape of an islet of closed contour, physically and electrically isolated from the remainder of the substrate, one of the sensor terminals being electrically connected to the islet;

it is provided between the operative area and the remainder of the substrate an interface including at least one peripheral lateral layer made of an electrically isolating material adapted to provide both a mechanical securing of the operative area to the substrate and an electrical isolation between the operative area and the substrate, the peripheral lateral layer being monolithically integrated with the remainder of the substrate and with the operative area, laterally encompassing the operative area over its whole periphery, and extending transversally over the thickness of the substrate.

According to various advantageous subsidiary characteristics:

the material of the first substrate and of the second substrate is a material belonging to the class of the biocompatible, biostable and corrosion-resistant materials, in particular titanium;

the electrically isolating material of the peripheral lateral layer is an oxide of the material of the metallic substrate;

the deformable operative area of the first substrate is located on a portion of the first substrate having a reduced thickness;

the operative area of the second substrate is an area located opposite the deformable operative area of the first substrate, the second transducer element is an element arranged on the inner face of the operative area of the second substrate opposite the first transducer element, and the first and second transducer elements are elements of one among a capacitive transducer, a resistive transducer and an inductive transducer;

the deformable operative area of the first substrate includes a piezoelectric layer, and the first and second transducer elements are opposite surfaces of the piezoelectric layer, including a surface in contact with the inner face of one of the substrates, and a free surface inside the sensor facing the inner face of the other substrate;

the sensor further includes an electronic component incorporated to the sensor and including a first component terminal and a second component terminal, and the at least one of the substrates includes: on its inner face, a recess accommodating the electronic component; another interface, including at least another peripheral lateral layer defining another islet isolated from the islet and from the remainder of the substrate; and an electrical connection from the first component terminal to the other islet, and an electrical connection from the second component terminal to the remainder of the substrate or to the islet;

the mechanical connection is a bonded connection between the first and second substrates, or it includes an intermediate sealing layer between the first substrate and the second substrate, in particular made of an electrically conductive material adapted to provide an electrical continuity between the first and the second substrate;

the at least one of the substrates includes, on its outer face, a surface isolating layer, with, in the islet area, at least one contact zone made exposed or left exposed;

in this latter case, the contact zone may protrude in the transverse direction with respect to the remainder of the outer face of the substrate, or two contact zones may be provided, with two respective protruding zones made exposed or left exposed, one in the islet area and the other in the area of the remainder of the substrate, and between the two protruding zones, in the area of the peripheral lateral internal layer, a recessed zone with an isolating layer.

Additional aspects of the invention will be set forth in part in the description which follows, and in part will be obvious from the description, or may be learned by practice of the invention. The aspects of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE SEVERAL VIEWS OF THE DRAWINGS

The accompanying drawings, which are incorporated in and constitute part of this specification, illustrate embodiments of the invention and together with the description, serve to explain the principles of the invention. The embodiments illustrated herein are presently preferred, it being understood, however, that the invention is not limited to the precise arrangements and instrumentalities shown, wherein:

FIG. 4 is a top view illustrating the successive steps (a) to (c) of the oxidation step of the first above-mentioned method, at one of the bridges of material visible in FIGS. 2 and 3.

FIG. 5 is a cross-sectional view of the structure of FIG. 3, after full completion of the oxidation step.

DETAILED DESCRIPTION OF THE INVENTION

First will be exposed various examples of feedthroughs for the making of a sensor according to the invention, as well as two methods of making such feedthroughs.

Feedthrough Structure

Figure 1:
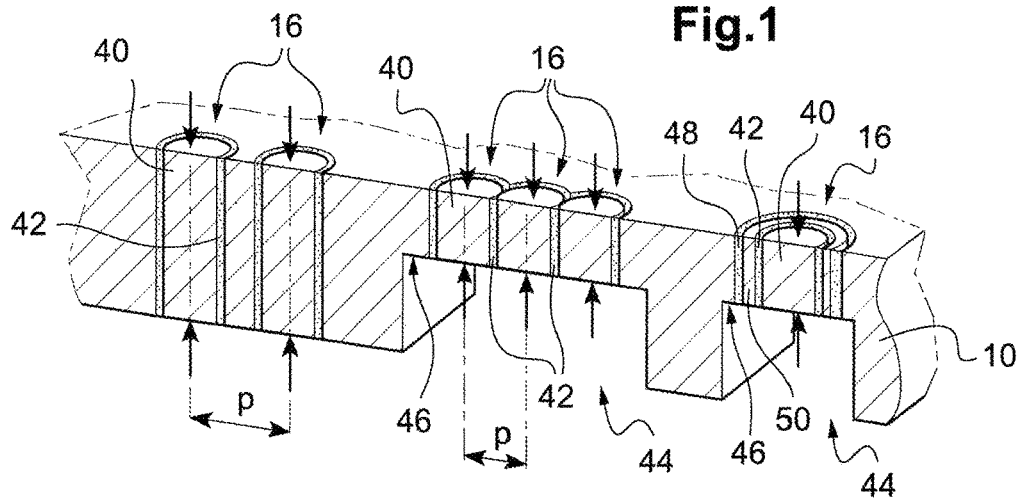
FIG. 1 is a cross-sectional view of feedthroughs for the making of a sensor according to the invention, showing various possible embodiment variants.

FIG. 1 is a cross-sectional view of substrate 10 showing several types of feedthroughs for the making of a sensor according to the invention, with the following variants:

on the left of the figure, making of two feedthroughs 16 through the totality of the thickness of the substrate 10 (thickness that may vary, typically but not limitatively, between 50 µm and 500 µm), these two feedthroughs being close but not adjacent to each other;

in the centre, making of three adjacent feedthroughs 16, these latter being moreover made in a area of the substrate having a reduced thickness;

on the right, making of a simple feedthrough in a area of the substrate having a reduced thickness, with a structure providing a double isolation and/or allowing the potential integration of an integrated filtering or decoupling capacitive component.

In the figures, the vertical arrows schematize the places where it will be possible to make the electrical contact arrangements on the through-element of each feedthrough 16, on either side of the substrate, according to techniques known per se, that will be briefly described hereinafter, in particular with reference to FIGS. 6 and 7.

Each feedthrough 16 includes a metal through-element 40, which is an element formed in the material of the substrate and extending transversely through the thickness of the substrate, from one face to the other of the latter. Laterally, the through-element 40 is arranged as an element in the shape of an islet of closed contour, physically and electrically isolated from the substrate.

It will be noted that, in the present description, the term "transverse" indicates a direction corresponding to the thickness of the substrate, hence perpendicular to the surface of the latter, whereas a "lateral" direction will qualify a direction extending along the extent of the substrate, in other words a radial direction with respect to a transverse axis of the feedthrough.

As regards the closed peripheral contour of the islet defining the feedthrough element, this contour may be of any shape: circular, polygonal (rectangular) or indifferent, since, due to its closed character, it fully isolates the islet from the remainder of the substrate, both physically and electrically (the term "peripheral" having to be understood as qualifying a islet that is structurally separated and electrically isolated from the remainder of the substrate).

Moreover, the generating line defining the contour of the islet does not necessarily extend perpendicular to the substrate: for example, the contour may be a cylinder of revolution, but also any cylinder, or also a cone (see in particular FIG. 3, in the centre), a pyramid, or of any shape.

The feedthrough further includes an interface for coupling the through-element 40 to the remainder of the substrate 10, which provides both the mechanical securing of this through-element to the substrate and the electrical isolation between through-element and substrate.

Characteristically, this coupling interface is provided by a peripheral lateral layer 42 made of an electrically isolating material, laterally encompassing the through-element 40 over its whole periphery and extending, transversely, through the thickness of the substrate.

The manufacturing techniques described below make it possible, in particular, to make a monolithically integrated unit including the substrate, the through-element and the lateral layer together, in which unit this lateral layer provides, essentially and directly, both i) the mechanical securing of the through-element to the substrate and ii) the electrical isolation between the through-element and the substrate, thanks to a direct and lateral (mechanical) junction of the through-element 40 with respect to the substrate 10.

Very advantageously, the material of the peripheral lateral layer 42 is an oxide of the metal constituting the substrate 10, in particular titanium oxide $TiO_2$: indeed, titanium and its oxide are materials that have the advantageous properties of biocompatibility, biostability and resistance to corrosion that make them particularly adapted to a very large number of applications, in particular for active medical devices in contact with corporeal tissues or fluids, especially implantable medical devices.

In the example illustrated on the left in FIG. 1, two similar feedthroughs 16 have been made in the same way, with a centre-to-centre pitch p that may be all the more reduced that the footprint in the lateral direction is that of a single through-element 40 with its lateral layer 42, without peripheral protrusion.

As illustrated in the central part of FIG. 1, the feedthrough(s) 16 may be made on a portion 44 of the substrate having a reduced thickness, wherein this reduced portion is hollowed out from the lower face of the substrate 10 according to techniques that will be described hereinafter, in particular with reference to FIG. 8.

Still in the example illustrated in the centre of FIG. 1, a plurality of feedthroughs 16 are illustrated, formed with their peripheral lateral layers 42 adjacent to each other (i.e. an isolating oxide layer may be common to two adjacent feedthroughs in the area in which these latter are the closest to each other), which makes it possible to reduce even more the centre-to-centre pitch p between adjacent feedthroughs.

In the case where a portion 44 with a reduced thickness is formed, there may be, or not, a recess or shoulder 36 between the peripheral lateral layer 42 and the lateral edge of the reduced-thickness portion 44 having a reduced thickness.

On the right in FIG. 1 is shown an example of a simple feedthrough including two concentric peripheral lateral layers 42, 48 (the term "concentric" being understood in the broader meaning, that is to say that an external layer 48 fully surrounds an internal layer 42, the contours of these layers being not necessarily coaxial, nor even circular).

Having several peripheral lateral layers makes it possible in particular to maximize the electrical isolation between the through-element 40 and the remainder of the substrate 10.

This configuration also makes it possible to physically space apart the through-element 40 and the remainder of the substrate 10, which may be interesting in certain applications such as the radiofrequency applications, in which is it important to reduce the electromagnetic coupling between neighbouring structures. In particular (and both for this embodiment and for the others), the through-element 40 can not only constitute a feedthrough, but also an isolated radiofrequency transmitting/receiving antenna, remote from the remainder of the substrate 10. In such a case, the element 40 will be able to adopt any known antenna geometric shape, such as loop, zigzag, spiral, fork, etc.

Reference may be made in particular to EP 2 873 437 A1, which describes such a type of RF component integrated to a substrate and connected to a monolithically integrated feedthrough made through this substrate.

This configuration also makes it possible, by a suitable choice of the size of the peripheral lateral layer, to make an integrated filtering or decoupling capacitor structure able to be associated with the feedthrough: indeed, the alternation of the concentric metal/oxide/metal layers corresponds to a frame/dielectric/frame structure of a capacitor, the intermediate layer acting as a dielectric. This is the case of the respective layers:

40/42/10 (as on the left in FIG. 1), or

40/42/50 and 50/48/10 (as on the right in FIG. 1).

The parameters of this capacitor (capacitance, breakdown voltage) can be modulated by a suitable choice of the thickness of isolating material and of the size of the through-element (surface of the peripheral contour and length in transverse direction).

These parameters may be chosen as a function of the technical objective : either to make a controlled coupling with the substrate (for example, for filtering purpose), or on the contrary to decouple as far as possible the feedthroughs from the substrate. In this latter case, it may in particular be advantageous to increase the number of concentric interfaces (as on the right in FIG. 1, where these concentric interfaces are two in numbers) because, in this case, the capacitances (undesirable) are electrically in series, which divides in proportion the whole coupling capacitance between the substrate 10 and the main through-element 40—in particular when the latter also provides an antenna function.

First Example of a Method of Making a Feedthrough Structure

With reference to FIGS. 2 to 8, a first method will now be described, which makes it possible to obtain a feedthrough structure according to the different variants illustrated in FIG. 1.

Figure 2:
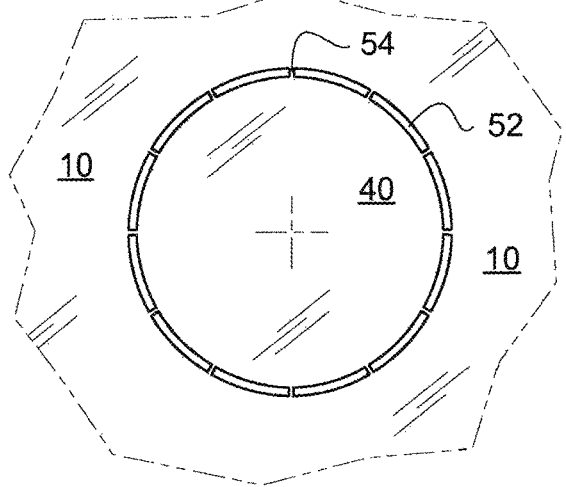
FIGS. 2 and 3 are top and cross-sectional views, respectively, illustrating a first method of making feedthroughs such as those illustrated in FIG. 1, according to different possible configurations, in an initial step after engraving of the substrate and before oxidation of the latter.
Figure 3:
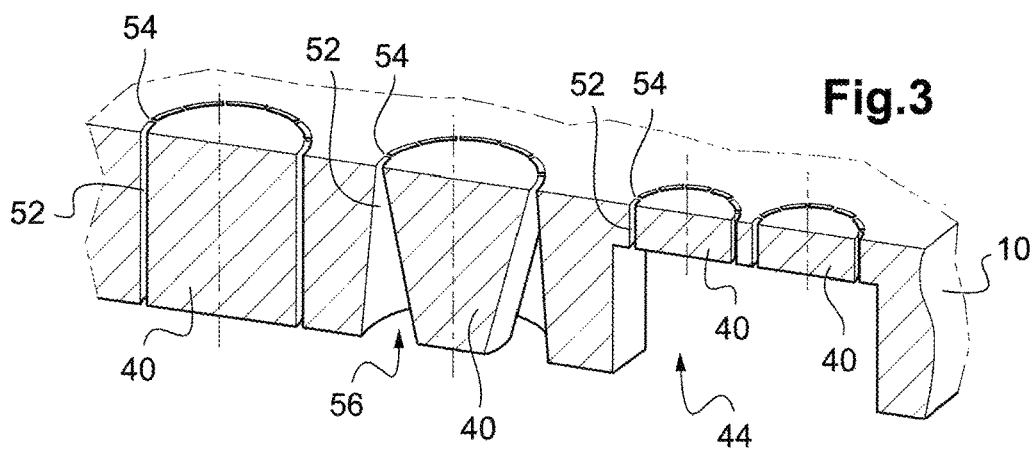

The first step of this method consists, as illustrated in FIGS. 2, 3 and 4(*a*), in engraving the substrate 10 by hollowing out, over its thickness, a through-trench 52. Laterally, the contour of this trench defines a central islet corresponding to the through-element 40 of the feedthrough to be made.

The through-trench 52 extending right through the thickness of the substrate, so as to be able to keep the central element 40 in place, it is provided to leave thin radial bridges 54 of non-engraved material. The number and the configuration of these bridges or arms of non-engraved material may be included between 1 and a number as high as desirable, wherein these bridges can be symmetrical or not, and regularly distributed or not.

At this stage, the central element is kept mechanically coupled to the remainder of the substrate by the bridges 54, but it is not electrically isolated from the substrate because the bridges leave a conductive path. There is not either any hermeticity through the structure between the central element 40 and the remainder of the substrate 10, because the sectors of the trench 54 are engraved all the way through either side of the surface and leave an open free inner volume, visible in particular on the enlarged representation of FIG. 4(*a*).

FIG. 3 illustrates various possible embodiment variants of the through-trench 52.

On the left in FIG. 3, the trench 52 is a trench with two parallel opposite walls, the trench further extending through the whole thickness of the substrate.

In the centre of FIG. 3, a variant is represented, in which the opposite walls of the trench are not parallel, the trench having a larger width in 56 on the side of one of the faces of the substrate (this non-parallelism may in particular be introduced by the manufacturing method that generates a penetration angle, which may be true in all the configurations). That way, the bridges of material 54 extend now over only a fraction of the thickness of the substrate, unlike the variant represented on the left in FIG. 3.

On the right in FIG. 3, another variant is represented, in which the feedthrough is made in a portion 44 of the substrate having a reduced thickness, which makes it possible, here again, to reduce the length in transverse direction of the bridges of material 54 (and also that of the central element 40). This variant may be made in two different manners:

in a first sub-variant, the substrate is first thinned down in the area 44, to provide it with a reduced thickness, then the trench 52 is made as described hereinabove, i.e. by hollowing out a through-trench opening into the lower face of the thinned area 44;

in a second sub-variant, a blind trench is hollowed out in the substrate over a fraction of its thickness, then the substrate is thinned down to make the area 44 with a reduced thickness, over a sufficient depth to reach the blind trench 52 that had been hollowed out from the other side of the substrate and hence to make the latter a through bore.

The hollowing out of the through-trench 52 has hence allowed shaping the central islet corresponding to the through-element 40, the latter being kept in place by the bridges of material 54. This situation corresponds to that of FIGS. 4(*a*).

The following step, illustrated in FIGS. 4(*b*), 4(*c*) and 5, consists in making simultaneously the electrical isolation and the hermeticity of the central element 40 by a step of controlled-thermal oxidation of the substrate.

This step will produce, concurrently:

in depth, the growth of a front of isolating oxide consuming the metal of the substrate (that of the central element 40 as well as that of the remainder of the substrate 10), as illustrated in 58 in FIG. 4(*b*), where the initial place of the trench before oxidation is represented in dotted line in 52; and at the surface, the growth of a thickness of oxide on the walls of the trench 52, as illustrated in 60 in FIG. 4(*b*).

The continuation of the controlled oxidation will entail a progressive filling of the free inner volume remaining between the two opposite walls of the trench 52, up to the complete filling of this free volume, as illustrated in FIG. 4(*c*).

Moreover, the peripheral size of the linking arms 54 has been chosen small enough so that, once the phase of complete filling completed, the metal of the bridge of material 54 is entirely transformed into oxide, as also illustrated in FIG. 4(*c*). The two opposite fronts on either side of the bridge of material 54 have joined each other, hence electrically isolating the central element 40, and making it hermetic, relative to the remainder of the substrate 10.

On the left of FIG. 5 is illustrated, in cross-sectional view, the structure obtained in the case of a trench of constant width (configuration corresponding to that illustrated on the left in FIG. 3).

On the right of FIG. 5 is illustrated the structure obtained in the case where a trench of variable width had been hollowed out (configuration corresponding to that illustrated in the centre of FIG. 3): the filling of the trench is then made only over a portion of the thickness of the substrate, chosen so as to provide the required level both of mechanical securing of the central element 40 to the substrate 10 and of electrical isolation of this through-element 40 with respect to the substrate 10. If the mechanical strength is not sufficient, the thermal oxidation may be continued up to filling the remaining cavity 56 over its whole depth, or the latter will be filled by deposition of a third-party, isolating or conductive, material.

The following step consists in making an electrical connection arrangement on the central element 40.

Indeed, the latter is electrically isolated from all sides, in particular by the upper oxide layer 62, and likewise on the opposite side by the lower oxide layer. It is hence necessary to make, at the through-element 40, an electrical continuity between the two faces of the substrate to constitute the electrical connection of the feedthrough.

The electrical connection arrangement (in this embodiment as in all the others) may be made on either one of the two faces—upper and lower—of the central through-element 40, with transfer or deposition of a conductive connection element (added wire, track on the surface of the substrate, etc.) intended to provide an electrical connection with distant elements, circuits or components located on either side of the substrate. But the electrical connection arrangement may be made on only one face of the through-element, the other face of the through-element being a directly usable active face, to constitute for example a surface electrode applied on one face of a device casing, or also on a sensor integrated to a device. This configuration is particularly advantageous for making an implantable device in which this surface electrode is intended to come into contact with a tissue of the patient into whom the device has been implanted.

In all the cases, it is advisable to make exposed or leave exposed each of the upper and lower faces of the central through-element 40.

A first solution consists, before the oxidation, in depositing an oxidation inhibitor material such as, for example, titanium nitride, silicon nitride, tungsten, platinum, niobium or palladium, or any combination of these materials, over a thickness of a few tens to a few hundreds of nanometres, in the areas of the substrate surface in which it is desired to see the oxide grow. The electrical contact is then directly obtained after oxidation and elimination of the inhibitor layer, with possibly later deposition of an additional layer of a metallic material such as gold, platinum, palladium, niobium, iridium, or any combination of these materials.

Figure 6:
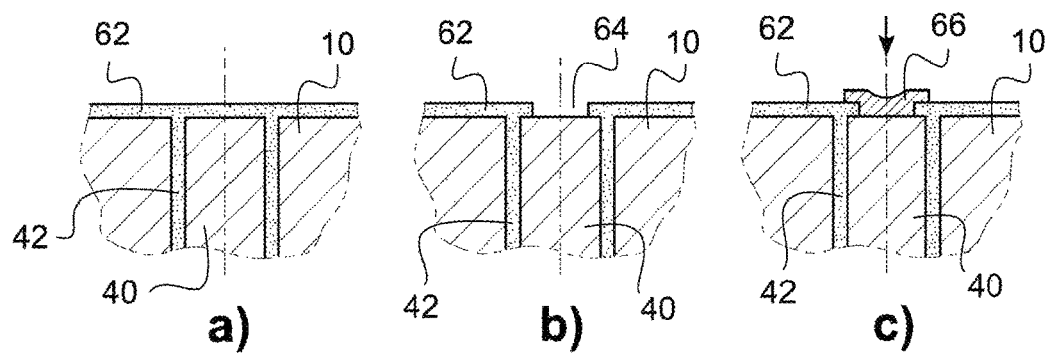
FIG. 6 is a cross-sectional view illustrating the successive steps (a) to (c) of making of an electrical contact on the through-element, according to a first possible technique of electrical contact arrangement.

Another solution, illustrated in FIG. 6, consists, after completion of the oxidation (FIG. 6(*a*)), in eliminating locally the oxide layer, for example by plasma or laser engraving, up to make the surface of the metallic material of the central element 40 exposed, as illustrated in 64 in FIG. 6(*b*).

The so-exposed electrical contact zone may, here again, be optimized by deposition, as illustrated in 66 in FIG. 6(*c*), of an additional metal layer made of a material such as gold, platinum, palladium, niobium, iridium or any combination of these materials. This additional metal layer may, laterally, either been confined to the area 64 without oxide, or protrude from the latter and cover the oxide beyond the periphery of the zone 64 (as illustrated in FIG. 6(*c*)).

Figure 7:
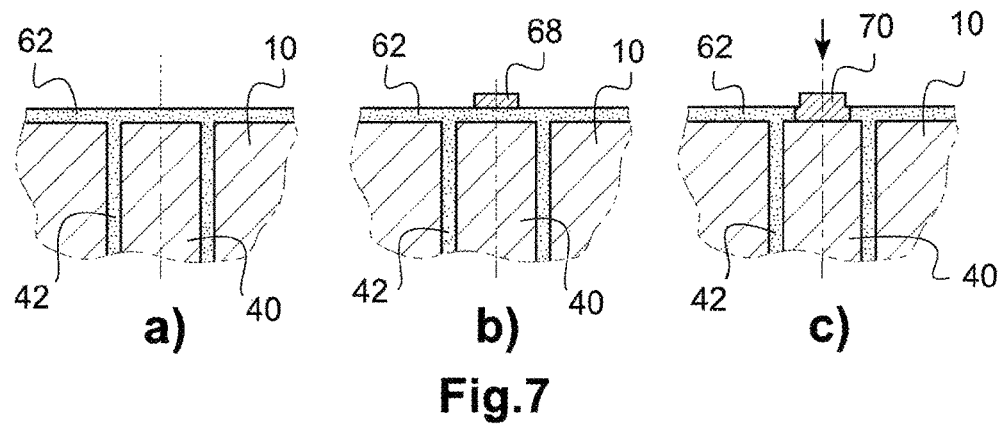
FIG. 7 is a cross-sectional view illustrating the successive steps (a) to (c) of making of an electrical contact on the through-element, according to a second possible technique of electrical contact arrangement.

Still another possibility of making the electrical contact arrangement is illustrated in FIG. 7.

After the step of oxidation of the substrate (FIG. 7(*a*)), a layer of a suitable material, such as gold, platinum, palladium, niobium, iridium or any combination of these materials, is deposited above the zone in which it is desired to make the contact, as illustrated in 68 in FIG. 7(*b*). A heat treatment then generates a diffusion of this material in the oxide, as illustrated in 70 in FIG. 7(*c*), which has for effect to make this oxide conductive in the underlying zone.

These different techniques of making an electrical contact arrangement are known per se and won't be described in more detail. They may be implemented in the same way on the other side of the substrate, so as to define an electrical continuity between the two faces, inner and outer, of the through-element and to hence make the electrical connection (or each electrical connection) of the feedthrough.

Figure 8:
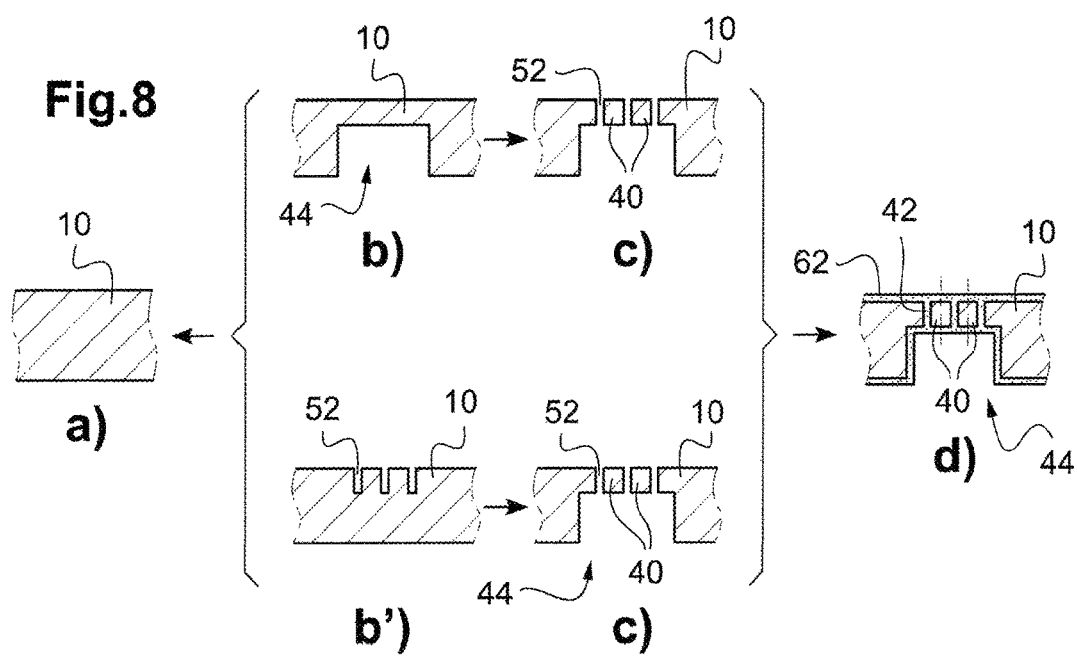
FIG. 8 is a cross-sectional view illustrating, according to two possible variants, the different steps (a) to (d) of making of a feedthrough by the first above-mentioned method, in the case where a thinning of the substrate is provided in the area of the feedthrough.

FIG. 8 schematically illustrates the making of a feedthrough on a zone 44 of the substrate having a reduced thickness, according to two variants that had been described hereinabove as regards the hollowing out of the trench: previous hollowing out the portion 44 having a reduced thickness, then of the through-trench 52 (FIGS. 8(*a*) to 8(*c*)); or previous hollowing out of blind trenches 52, then hollowing out of the substrate to obtain the portion 44 with a reduced thickness up to reach the trenches 52 and to make them through-going (FIGS. 8(*a*), 8(*b*') and 8(*c*')).

These steps according to either one variant are then followed with the step of oxidation of the substrate (FIG. 8(*d*)) making it possible to obtain the desired structure for making feedthroughs in the area 44 of the substrate with a reduced thickness.

Second Example of a Method of Making a Feedthrough Structure

A second method making it possible to obtain a feedthrough structure will now be described with reference to FIGS. 9 to 12.

Figure 9:
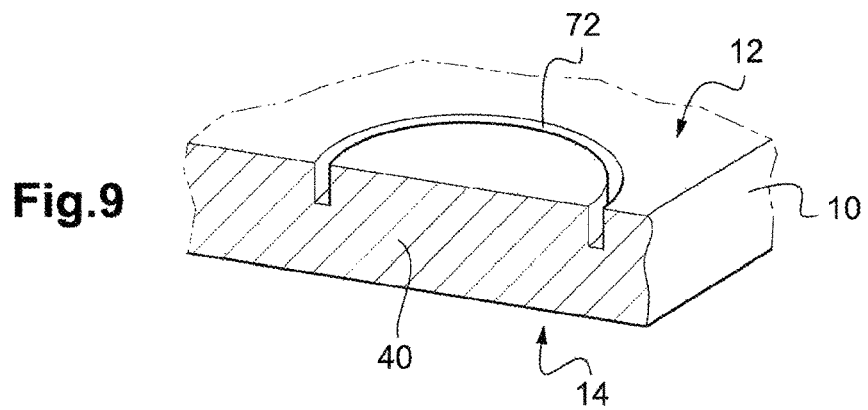
FIGS. 9 to 12 are cross-sectional views illustrating the different successive steps of a second above-mentioned method of making of a feedthrough.

The first step, illustrated in FIG. 9, consists in shaping an islet (corresponding to the through-element of the feedthrough to be made) by hollowing out from the material of the substrate, from a first face of the latter, for example the upper face 12, of a blind trench 72 extending transversally over a fraction of the thickness of the substrate 10. Laterally, this trench extends over the whole periphery of the central islet 40—that is to say that the trench 72 does not leave bridges of material, unlike the trench 52 illustrated in FIG. 2 of the preceding method.

Figure 10:
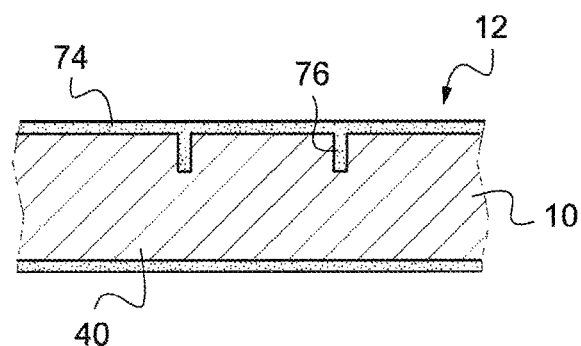

The following step, illustrated in FIG. 10, consists in performing a controlled oxidation of the substrate material, including an oxidation of the lateral walls of the trench up to filling all or part of the free inner volume of the latter by oxide growing.

At the end of this oxidation step, the substrate includes on either one of its faces a layer of oxide coating 74 (typically of a few micrometres of thickness) extending, on the side of the upper face 12, along the trench 76 that is fully filled (as illustrated in FIG. 10) or only partially filled. In the case of a partial filling, the filling may be optionally made complete by the later deposition of an isolating or conductive filling layer, so as, in particular, to mechanically reinforce the structure.

Figure 11:
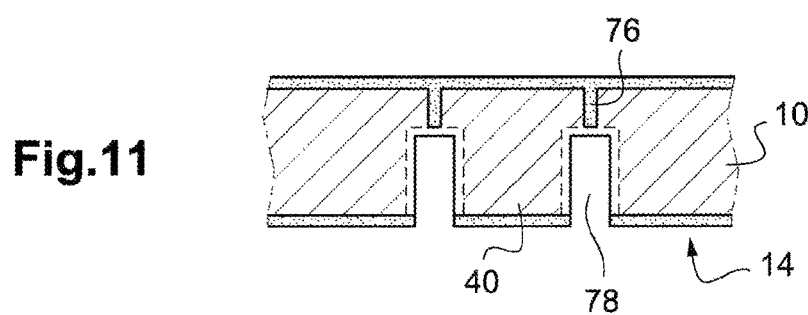

The following step, illustrated in FIG. 11, consists in hollowing out a peripheral groove 78 from the other face of the substrate, i.e. the lower face 14 in the illustrated example. This peripheral groove 78 may be hollowed out over a depth allowing it to reach the oxidized trench 76 and hence fully isolate the central through-element 40.

To avoid that an over-engraving damages the isolating oxide of the filled trench 76, an advantageous variant, illustrated in FIG. 11, consists in stopping the hollowing out of the groove 78 a little before reaching the filled trench 76 then completing the engraving by a more selective chemical etching, illustrated in dotted line in FIG. 11, this selective etching essentially attacking the metallic substrate 10 but very little the oxide of the filled trench 76.

However, given the engraving depth tolerances between the edge and the centre of a same wafer carrying a very large number of distinct components, certain places may be engraved more deeply than others.

Figure 12:
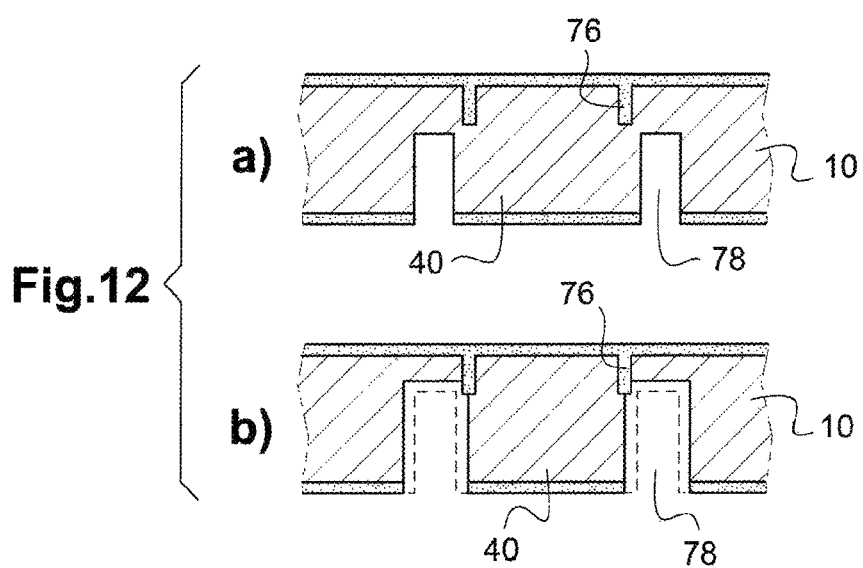

To address this drawback, and to avoid a substantial over-engraving that would excessively widen the desired dimensions, in particular in the lateral direction, it is possible, as illustrated in FIG. 12, to laterally offset the engraving of the groove 78 with respect to the position of the filled trench 76.

This offset in the lateral direction may be made either towards the inside or, as illustrated in FIG. 12(*a*), towards the outside, wherein the depth of the engraved groove 78 can be lower than, equal to or higher than the level of the bottom of the filled trench 76 located opposite.

Then, as illustrated in dotted line in FIG. 12(*b*), an isotropic, chemical or physical, engraving of the metal, propagating in all the directions makes it possible, in all the configurations, to reach the oxide of the filled trench 76 and to electrically isolate the central through-portion 40 with respect to the remainder of the substrate. The depth of the isotropic engraving of the metal is typically of the order of 15 to 20 µm.

Indeed, the tolerances of alignment between front face and rear face of a same wafer are very homogeneous and very low (typically from 1 to 5 µm) whatever the position of the component on the wafer, which reduces the required depth of isotropic engraving.

The advantage of this latter variant is its reduced sensitivity to the engraving depth tolerances, because it is sufficient to reach a minimum proximity with respect to the oxide of the filled trench 76 to compensate for the size variations linked to the manufacturing tolerances.

Generally, and whatever the embodiment variant implemented, it will be noted that the isolating oxide layer present on each face of the substrate has no longer any function, neither electric nor mechanical. From then on, this oxide layer may be fully or selectively engraved to make the metal at the surface of the substrate exposed. The exposed metal can be used for various purposes such as electrical contact with the substrate, bonding the piece made on another element of the device, integration of an integrated circuit chip, etc.

FIGS. 13*a*, 13*b*, 14*a* and 14*b* are cross-sectional views illustrating, according to two different implementation possibilities, a variant of the method of FIGS. 9 to 12, at the stage of the method in which the blind trenches 72 and 78 have just been engraved (FIGS. 13*a* and 13*b*) and after the completion of the step of controlled oxidation of the substrate material, respectively.

Figure 13A:
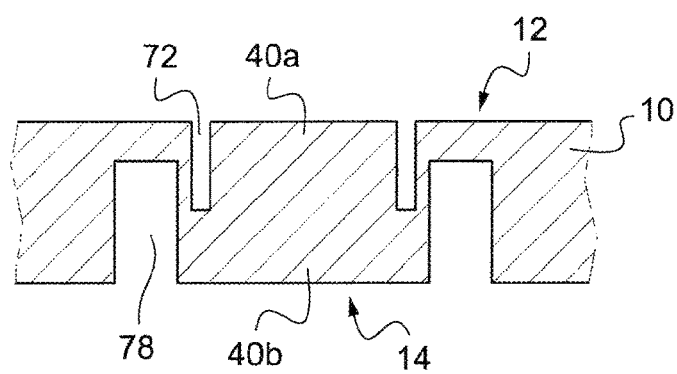
FIGS. 13a and 13b are cross-sectional views illustrating, according to two respective possibilities of implementation, a variant of the method of FIGS. 9 to 12, at the stage of the method in which the blind trenches have just been engraved.
Figure 13B:
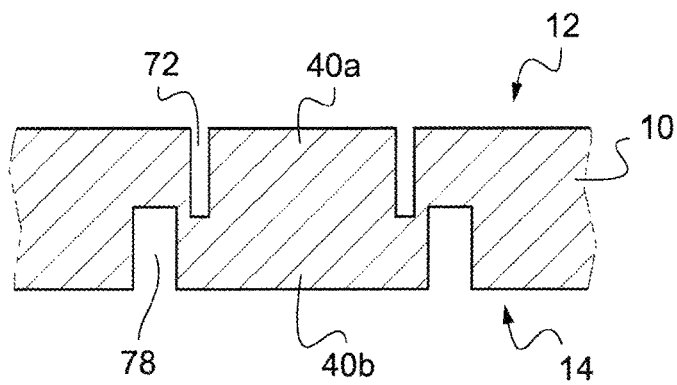

In this variant, in which a trench 72 engraved on a face is offset with respect to a trench 78 engraved on the other face, the electrical isolation between the engravings (and hence between the central islet and the remainder of the substrate) is established by an oxidation 76 of the interstice between these two trenches. This may be made either by engraving of two offset trenches 72, 78 on the opposite faces with vertical overlapping (FIG. 13*a*), or by engraving of two offset trenches 72, 78 on the opposite faces and in vertical proximity (FIG. 13*b*).

The order of making of the engravings 72, 78 on one face then on the other is indifferent. The trenches may be offset in different directions (inward offset, outward offset, overlapping offset). Each of the trenches 72, 78 defines a respective islet 40*a*, 40*b* and these two islets, when they will be electrically isolated together from the remainder of the substrate, will form the central conductive element 40 of the feedthrough.

The trench engraving depth must be sufficient on either side to define a very fine separation between both (whose size may vary, typically but non-limitatively, between 0.5 µm and 25 µm). They may be either in overlapping (FIG. 13*a*) or in proximity (FIG. 13*b*).

The offset defining the gap between the two trenches will be thin enough so that this gap is fully oxidized (as in 76 in the figures), hence becoming electrically isolating.

Figure 14A:
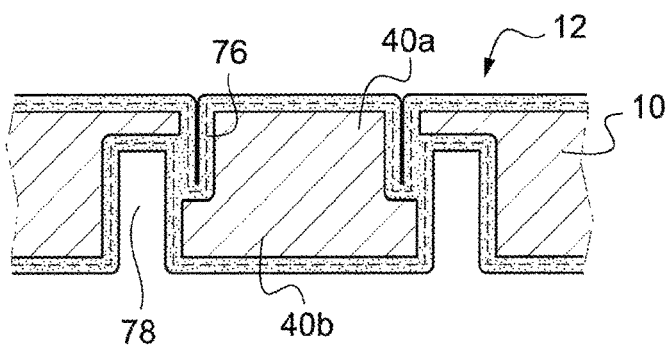
FIGS. 14a and 14b are similar to FIGS. 13a and 13b, after completion of the step of controlled oxidation of the substrate material.
Figure 14B:
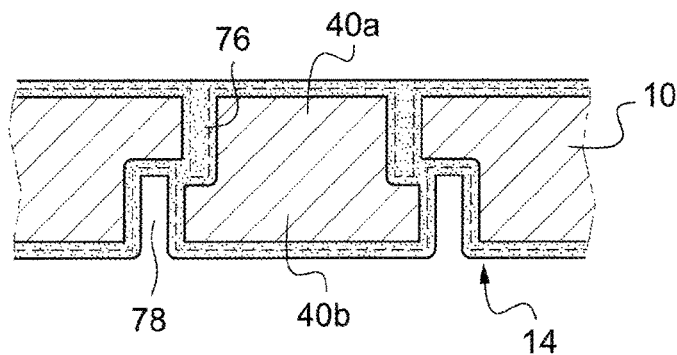

In the implementation illustrated in FIG. 14*b*, one at least of the two trenches (the trench 72 of FIGS. 14*a* and 14*b*) may be narrow enough so that its volume is fully filled by the oxide during the thermal oxidation (as in 76 in FIG. 14*b*). If this is not the case (as illustrated in FIG. 14*a*), the free residual volume of the oxidized trench(es) may be filled—or not—by the later deposition of another material, so as to rigidify the structure.

Sensor Structure According to the Invention

A sensor structure according to the invention will now be described, with reference to FIGS. 15 to 21, which illustrate various embodiment variants.

The basic idea of the invention consists in benefitting from the excellent performances of mechanical strength and electrical isolation of the above-described "feedthroughs" (hermetic passages, electrically isolated from an electrical connection through a metallic wall) for the making of a sensor in which the totality of the structure is made from a metallic material, very advantageously a perfectly compatible material such as titanium.

Essentially, the sensor of the invention is made from two distinct substrates of this metallic material during the preliminary steps of making the various elements carried by each of the two substrates, according to the technologies of fabrication that are conventional per se.

In particular, each of the two substrates carries a respective transducer element, typically an electrode and an opposite counter-electrode: one of the substrates includes the deformable operative area (membrane or other) coupled with the first transducer element (the electrode), whereas the other substrate carries the other transducer element (the counter-electrode), which is fixed, so as to vary between these two elements an electrical parameter that will then be able to be transformed into a sensor signal.

In this configuration, the electrode and the counter-electrode are connected to two respective terminals of the sensor, which are two areas of either substrate in electrical continuity with the electrode and the counter-electrode.

The isolation between these two sensor terminals is obtained by the above-described technology of vertical isolation of feedthrough: the matter is to make, on either one of the substrates (or on both of them) an interface including at least one peripheral lateral layer making it possible to isolate the two terminals of the sensor, which are each in electrical continuity with one of the respective transducer elements.

This electrode/counter-electrode configuration is however not limitative, and other transducer configurations are conceivable, in particular, as will be described hereinafter, using a piezoelectric layer producing between its faces a variable electric potential as a function of the mechanical stress that is applied thereto. In this case, the two faces of the layer are connected to respective terminals of the sensor, and the interface of the peripheral lateral layer has for function to isolate from each other the two terminals and their connections to the piezoelectric element.

Figure 15:
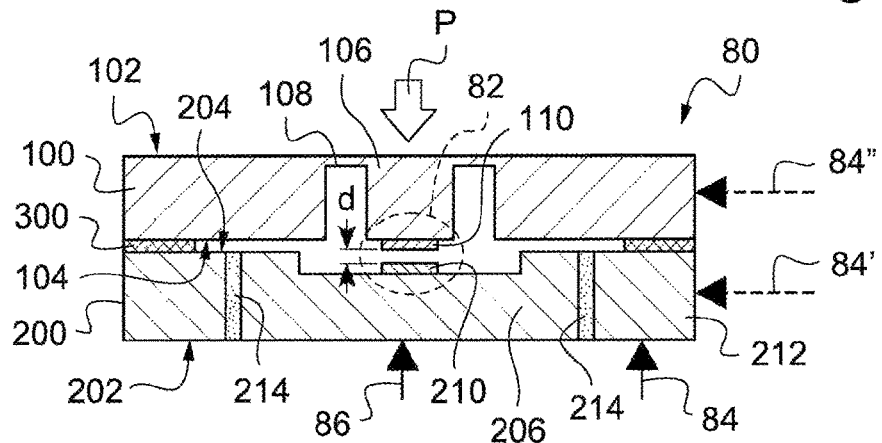
FIG. 15 is a cross-sectional view of a sensor according to the invention.

FIG. 15 illustrates an example of sensor made according to the teachings of the invention.

The sensor 80 essentially includes two distinct substrates 100 and 200, typically made from a biocompatible, biostable and corrosion-resistant material, such as titanium.

The substrate 100 includes an outer face 102 and an inner face 104, and the second substrate includes an outer face 202 and an inner face 204.

The faces 104 and 204 are arranged opposite to each other, whereas the outer face 102 of the substrate 100 directly receives a stress, for example a pressure P from a surrounding fluid in contact with the outer face 202, which has for effect to deform a central element 106 of the substrate surrounded by a thin deformable peripheral membrane 108.

Advantageously, in this embodiment as well as in those that will be described hereinafter, if the outer face 102 of the substrate 100 is directly exposed to a corporeal fluid such as blood (for example, in the case of a device sensor implantable in situ, accommodated in a cavity of the heart), this outer face 102 may be subjected to a surface micropatterning or nanopatterning, in order to reduce at this place the phenomena of cellular colonization liable to modify the sensor performances over the long term.

The central portion 106, hereinafter also called "operative area" of the substrate 100, includes on the inner face 104 of the substrate a first transducer element, typically an electrode 110, which moves transversely according to the variable stresses, for example variations of the pressure P undergone on the outer face 102 in the area surrounding the deformable thinned portion 108.

The substrate 200 includes an area 206, hereinafter also called "operative area" of the substrate 200. This operative area is located opposite the central portion 106 of the substrate 100 and it includes a second transducer element 210 such as a counter-electrode.

It will be noted that the electrodes 110 and/or 210 may be added electrodes or, as a variant, consisted by the surface itself of the substrate 100 or 200, if the conductivity of this substrate is sufficient.

The two substrates 100 and 200 are combined together by a mechanical connection 300. This mechanical connection may be obtained directly by putting the two substrates in contact, with adhesion by electrostatic effect (Van der Waals force) or by thermal bonding, thermomechanical bonding or another conventional method for wafer bonding.

It is also possible to provide, for the mechanical connection 300, an intermediate layer made of a third-party material such as platinum, titanium oxide, titanium nitride or alumina, and combinations of the preceding materials.

The electrode 110 and the counter-electrode 210 form together a transducer 82 with two poles, one of the poles (the electrode 110) being connected to a first sensor terminal 84 and the other pole (the counter-electrode 210) being connected by a second sensor terminal 86.

These terminals 84, 86 being in electrical continuity with the material of the substrate 100, it is necessary to isolate them from each other, which is obtained by an interface including a peripheral lateral layer 214 made in the same way, and with the different possible variants, as the peripheral lateral layer 42 of the various feedthroughs described hereinabove with reference to FIGS. 1 to 8.

Hence, for the sensor 80 of FIG. 15, the isolating peripheral layer 214 electrically isolate the central operative area 206 of the substrate 200 (to which is connected the first sensor terminal 86) from the remainder 212 of the substrate (to which is connected the second sensor terminal 84), while providing a perfect mechanical securing between the two areas 206 and 212 of the substrate 200.

It will be noted that, in the example illustrated in FIG. 15, as well as in the following figures, the interface with the peripheral lateral layer 214 is made on the substrate 200. But this interface could also be, as a variant or as a complement, made on the substrate 100, since the matter is to provide a reliable and efficient isolation between the two transducer elements, herein the electrode 110 and the counter-electrode 210.

It will moreover be noted that an isolation that would be based only on an intermediate isolating sealing layer 300 would not be sufficient to obtain the desired performances. Indeed, this sealing layer 300 being very thin, in the practice, short-circuits may be established, in particular due to external pollutions linked to the machining method (in particular during the cutting of the chips) and/or conditions of use, where impurities or conductive crystals may create an electrical bridge between the two substrates.

The variation of the interval d between the two transducer elements 82 (the electrode 110 and the counter-electrode 210) may be measured by different techniques known per se:

capacitive measurement between the electrode 110 and the counter-electrode 210 (without contact between these electrodes, or with mechanical contact, wherein the electrode 110 can come into abutment against the counter-electrode 210: in this latter case, an additional isolating layer may be added one either one of the electrodes);

resistive measurement between the electrode 110 and the counter-electrode 210, the mobile electrode 110 coming successively into contact with a series of fixed counter-electrodes arranged in a star or in a concentric arrangement, formed on the substrate 200, so as to establish electrical bridges: the deformation of the membrane 108 causes a physical contact between electrode and counter-electrodes, with a variable number of electrical bridges as a function of the external stress undergone;

piezoelectric measurement, thanks to a piezoelectric layer deposited on the internal surface of the membrane 108: the deformation of the membrane generates between the two faces of the piezoelectric layer a variable electric potential that may be collected via a simple electrical contact taken at the metallic substrate in continuity with the electrical layer. In this case, the transducer no longer includes any counter-electrode. But, to measure a potential difference between the two faces of the piezoelectric layer deposited on the inner face of the substrate, two corresponding contacts are necessary, with a contact as described hereinabove (for the face of the piezoelectric layer in contact with the inner face of the substrate) and a contact on the free, opposite face, of the piezoelectric layer, turned inside the device.

Figure 16:
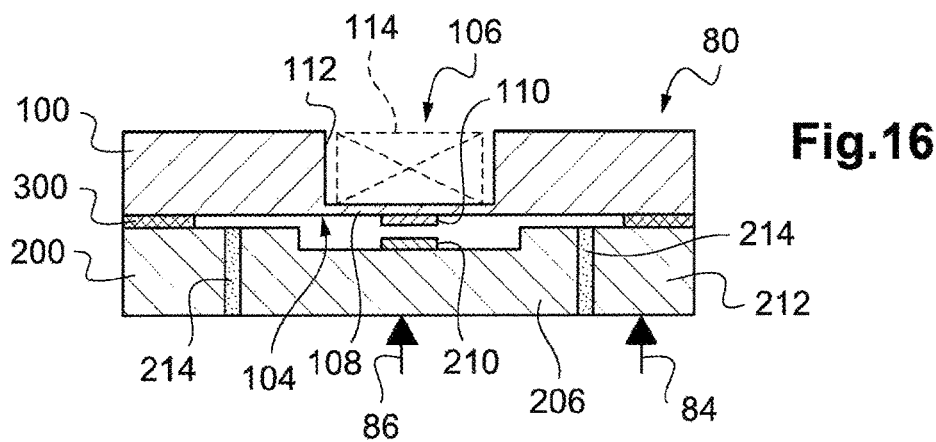
FIG. 16 is a cross-sectional view of an embodiment variant of the sensor of FIG. 15.

FIG. 16 illustrates a variant in which the substrate 100 includes a non-through recess 112, whose bottom constitutes the deformable membrane 108 that, in this case, is located at the level of the inner face 104 of the substrate 100.

In the case of an acceleration sensor or a microphonic sensor, the recess 112 can accommodate an added inertial mass 114 making it possible to increase the sensitivity of the sensor to the external stresses. The transfer of an inertial mass, which is heavier and hence generally made of a non-biocompatible material such as the tungsten, may also (and preferentially) be made from the configuration of FIG. 15, in which the membrane 108 is fully circular (no "embossment" at the titanium islet 106) and the added element is assembled to this membrane, hence remaining accommodated within the device, so as not to be subjected to biocompatibility constraints.

The membrane may be of any known geometry, circular, elliptic, rectangular, indifferent, planar or patterned, etc.

In any case, the structure of the invention makes it possible to entirely integrate to the sensor 80 the elements of the transducer 82, with very small dimensions and without having to provide an additional, biocompatible, external protective packaging.

The resulting sensor may be either an autonomous component (with which will be associated an integrated or remote electrical supply source), or an element of a more complex implantable device, for example a sensor integrated to the surface of the casing of an implantable device, or also be a component integrated into a detection/cardiac stimulation lead, hence benefiting from the electrical supply of the device.

Figure 17:
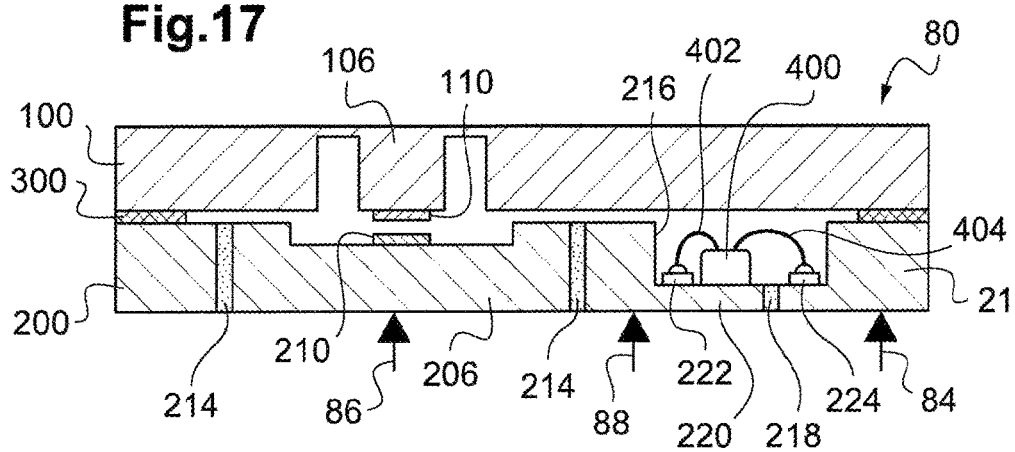
FIG. 17 is a cross-sectional view of a sensor such as that illustrated in FIG. 15, further incorporating therein an added electronic component.

FIG. 17 illustrates the possibility to incorporate to the sensor of the invention an additional electronic component 400 such as an electronic chip.

The basic structure is the same as that described hereinabove and illustrated in FIG. 15 or 16, and the component is placed in a cavity made in the substrate 200 (as the cavity 216 illustrated in FIG. 17), or in the substrate 100 according to the same principle.

The material of the chip, generally silicon, is not a biocompatible material but the chip will be entirely enclosed between the two substrates 100 and 200, which are made of a biocompatible material such as titanium.

The component 400 is connected to connection pads 222, 224, formed in the bottom of the cavity 216 of the substrate 200. These connection pads of the substrate 200 are connected by respective conductors 402, 404 to the terminals of the component 400 by known technologies such as, typically, wire bonding.

Beside the interface including the peripheral lateral layer 214, the matter is to create at least another interface including an additional peripheral lateral layer 218, made according to the same teachings as the layer 214. This additional interface creates an isolation between i) an additional isolated area 220 and ii) the operative area 206 connected to the first sensor terminal 86, as well as iii) the remainder of the substrate 212 connected to the second sensor terminal 84. A third sensor terminal 88 is connected to this additional isolated area 220, to make a connection to the component chip 400.

In the figures, the arrows show areas in which are made the electrical contact arrangements of the first and second sensor terminals 84 and 86 (and of the third terminal 88 in the case of FIG. 17).

The technique proposed by the invention makes it possible to make a direct electrical contact arrangement, by bonding or crimping a metallic element such as wire, ribbon or ring on corresponding zones of either one of the substrates 100 and 200.

It is advisable to make these electrical contact arrangements on zones that are not liable to induce on the sensor significant mechanical constraints, which could disturb the sensitivity of the latter by a permanent deformation that is difficult to control.

In particular, the contact of the sensor terminal 84 with the remainder of the substrate 212 out of the operative zone 206 may be made not only, as illustrated, through the outer mass 202 of the substrate 200, but also through the edge of the latter, as in 84', since the mechanical connection 300 between the two substrates is a connection that is conductive enough to provide the desired electrical continuity.

In all the cases, a metallisation may be added on the zone of the substrate to be contacted to facilitate the contact making, for example by deposition of a patch or a metallic layer made of a material such as gold, platinum, palladium, niobium, iridium, or any combinations of these materials.

Figure 18:
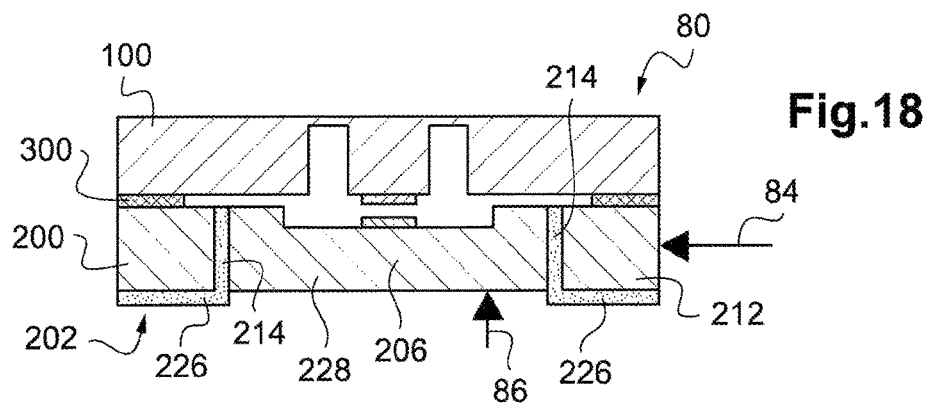
FIG. 18 is a cross-sectional view of an embodiment variant of the sensor of FIG. 15, with a surface-patterned isolating layer on one of its outer faces.

FIG. 18 illustrates an improvement of the sensor structure of FIG. 15 (this improvement being also applicable to the structure of FIG. 16), wherein a isolating oxide layer 226 has been selectively deposited on an outer face of a substrate, the outer face 202 of the substrate 200 in the illustrated example.

This isolating layer 226, made according to the same techniques as those described hereinabove in relation with FIGS. 1 to 14, makes it possible to delimit a first exposed contact zone 228 intended for the electrical contact arrangement of a first terminal 86 of the sensor. This zone is perfectly separated and isolated from the zone of the remainder of the substrate 212 on which is made the contact with the other sensor terminal, for example on the edge of the substrate 200.

The external isolating oxide layer 226 extends in surface the internal peripheral lateral layer 214 and is obtained, in the same way, by oxidation of the metal constituting the substrate 200: in the example described, an oxidation of titanium Ti into titanium oxide $TiO_2$.

Figure 19:
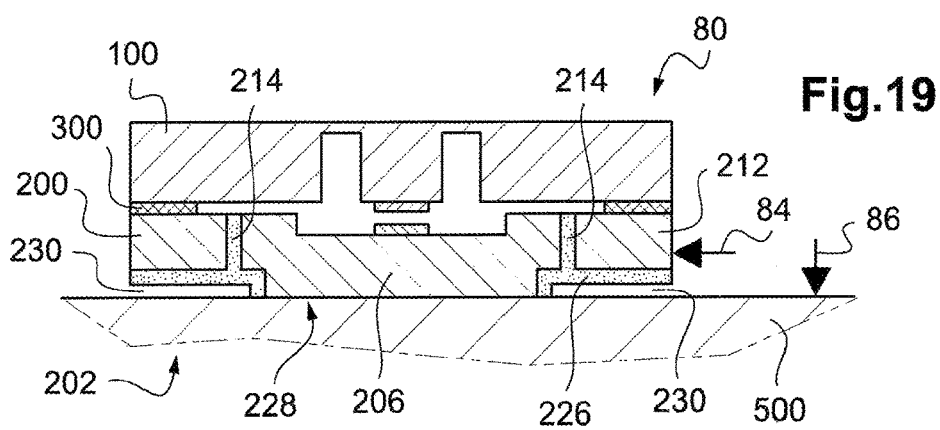
FIG. 19 is a cross-sectional view of an embodiment variant of the sensor of FIG. 18.

FIG. 19 illustrates a variant of the sensor of FIG. 18 in which the substrate 200 includes on its external face 202 a recessed zone 230, engraved during the steps of micromachining of the substrate. This zone 230 makes it possible in particular to make the contact with the zone 228 of the central operative portion 206 of the substrate with respect to the sensor on a support or another conductive substrate 500, that constitutes a pole connected to one of the terminals 86 of the sensor. The other terminal 84 is for example made by an electrical connection arrangement on the edge of the substrate 200.

Figure 20:
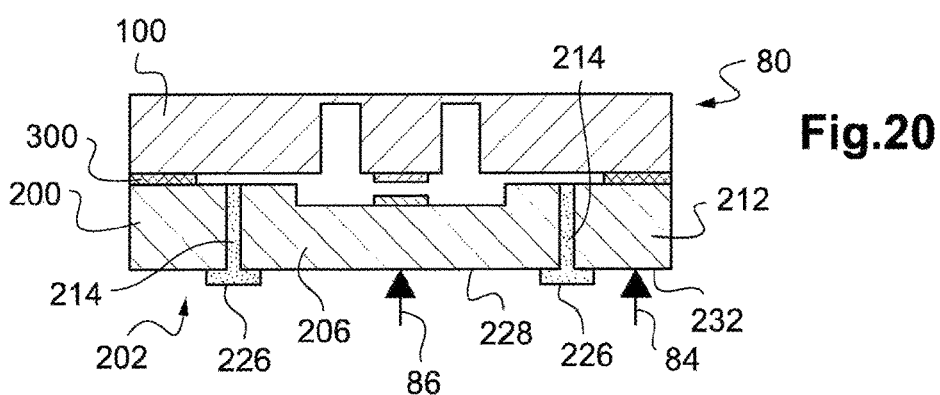
FIG. 20 is a cross-sectional view of another embodiment variant of the sensor of FIG. 18.

FIG. 20 illustrates a variant of the sensor of FIG. 18 making it possible to make, on a single and same face of the substrate 200 (the outer face 202), electrical contact arrangements for the sensor terminals 84 and 86. This may be interesting in particular when the sensor is integrated in an active implantable medical device of reduced size, such as a neurostimulator of very small thickness, or a so-called leadless cardiac stimulator directly implanted into a cavity of the heart.

The extent of the external isolating oxide layer 226 is reduced so as to leave exposed a second contact zone 232 above the area 212 of the remainder of the substrate. An electrical connection arrangement can hence be made from the outer face 202 of the substrate 200, both to the sensor terminal 86 (through the first contact zone 228 described hereinabove in FIG. 18) and to the other sensor terminal 84 (through the second, exposed, contact zone 232).

Figure 21:
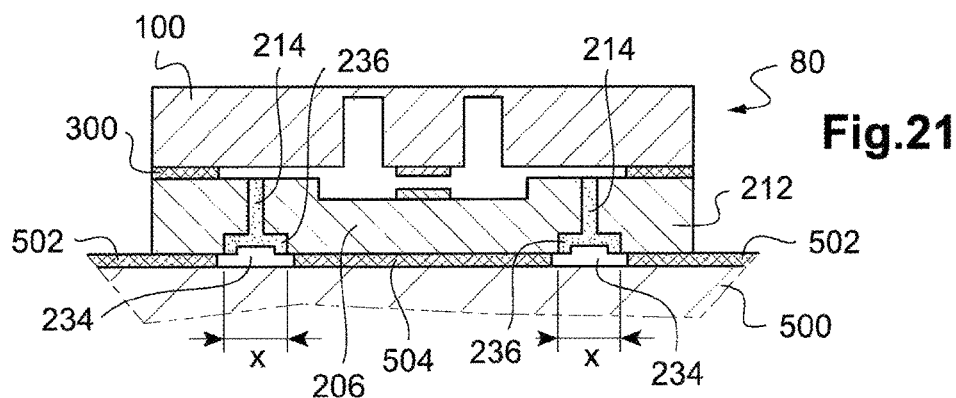
FIG. 21 is a cross-sectional view of an embodiment variant of the sensor of FIG. 19.

FIG. 21 illustrates a variant of the sensor of FIG. 19, in which recessed zones 234 are formed in the outer face of the substrate 200 in the vicinity of the internal peripheral lateral layer 214, leaving exposed this same face in the area of the central islet 206 and in the area 212 of the remainder of the substrate, and with the walls of the recessed zones 234 covered by the isolating oxide layer 236. This configuration makes it possible in particular to make electrical contact arrangements from a same face (the outer face) of the substrate 200, for example when the sensor 80 is added on a support or another conductive substrate 500 including conductive pads 502 and 504 that come directly in contact with the respective areas 206 and 212 of the substrate 200. It will be moreover noted that the isolation zone x between the two terminals of the sensor are easily modulatable by a suitable choice of the extent of the oxide layer formed in 236 on the walls of the recessed zones 234, wherein the oxide can, if necessary, protrude on the substrate, out of the cavity, to increase the distance of isolation x.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "includes" and/or "including," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

Having thus described the invention of the present application in detail and by reference to embodiments thereof, it will be apparent that modifications and variations are possible without departing from the scope of the invention defined in the appended claims as follows:

I claim:
1. A sensor comprising:
a first substrate made of a conductive material with an outer face and an inner face, comprising:
an operative area deformable under effect of a mechanical stress applied to the outer face, and
on the inner face, a first transducer element, mobile under the effect of a deformation of the operative area;
a second substrate made of a conductive material with an outer face and an inner face facing the inner face of the first substrate, and comprising an operative area;
a second transducer element adapted to cooperate with the first transducer element to vary an electrical parameter between the first and the second transducer element under the effect of said mechanical stress;
a mechanical connection for securing the first substrate to the second substrate, located outside the operative area of the first substrate the the operative area of the second substrate;
a first sensor terminal, electrically coupled to the first transducer element; and
a second sensor terminal, electrically coupled to the second transducer element, wherein, for at least one of the substrates:
the operative area extends transversally into the thickness of the substrate, from one face to the other of the latter;
the operative area has the shape of an islet of closed contour, physically and electrically isolated from the remainder of the substrate, one of the sensor terminals being electrically connected to the islet; and,
it is provided between the operative area and the remainder of the substrate an interface comprising at least one peripheral lateral layer made of an electrically isolating material adapted to provide both a mechanical securing of the operative area to the substrate and an electrical isolation between the operative area and the substrate,
the peripheral lateral layer being monolithically integrated with the remainder of the substrate and with the operative area, laterally encompassing the operative area over its whole periphery, and extending transversally over the thickness of the substrate.
2. The sensor of claim 1, wherein the material of the first and the second substrate is a material belonging to the class of the biocompatible, biostable and corrosion-resistant materials.
3. The sensor of claim 1, wherein the biocompatible, biostable and corrosion-resistant material is titanium.
4. The sensor of claim 1, wherein the electrically isolating material of the peripheral lateral layer is an oxide of the material of the metallic substrate.
5. The sensor of claim 1, wherein the deformable operative area of the first substrate is located on a portion of the first substrate having a reduced thickness.
6. The sensor of claim 1, wherein:
the operative area of the second substrate is an area located opposite the deformable operative area of the first substrate;
the second transducer element is an element arranged on the inner face of the operative area of the second substrate opposite the first transducer element; and
the first and second transducer elements are elements selected from the group consisting of a capacitive transducer, a resistive transducer and an inductive transducer.

7. The sensor of claim 1, wherein:
the deformable operative area of the first substrate comprises a piezoelectric layer; and
the first and second transducer elements are opposite surfaces of the piezoelectric layer, comprising a surface in contact with the inner face of one of the substrates, and a free surface inside the sensor facing the inner face of the other substrate.

8. The sensor of claim 1, wherein:
the sensor further includes an electronic component incorporated to the sensor and comprising a first component terminal and a second component terminal, and
said at least one of the substrates comprises:
on its inner face, a recess accommodating the electronic component;
another interface, including at least another peripheral lateral layer defining another islet isolated from the islet and from the remainder of the substrate; and
an electrical connection from the first component terminal to the other islet, and an electrical connection from the second component terminal to the remainder of the substrate or to the islet.

9. The sensor of claim 1, wherein the mechanical connection is a bonded connection between the first and second substrates.

10. The sensor of claim 1, wherein the mechanical connection comprises an intermediate sealing layer between the first substrate and the second substrate.

11. The sensor of claim 10, wherein the material of the intermediate sealing layer is an electrically conductive material adapted to provide an electrical continuity between the first and the second substrate.

12. The sensor of claim 1, wherein said at least one of the substrates comprises, on its outer face, a surface isolating layer, with, in the area of the islet, at least one contact zone made exposed or left exposed.

13. The sensor of claim 12, wherein the contact zone protrudes in the transverse direction with respect to the remainder of the outer face of the substrate.

14. The sensor of claim 12, comprising:
two contact zones, with two respective protruding zones made exposed or left exposed, one in the area of the islet and the other in the area of the remainder of the substrate, and
between the two protruding zones, in the area of the peripheral lateral internal layer, a recessed zone with an isolating layer.

\* \* \* \* \*